United States Patent

[19] Grit

[11] Patent Number: 5,948,124
[45] Date of Patent: Sep. 7, 1999

[54] COMPOSITION FOR DYEING HUMAN HAIR COMPRISING A CATIONIC DYE, A ZWITTERIONIC SURFACTANT, AND AN ANIONIC UV-ABSORBER

[75] Inventor: Mustafa Grit, Alsbach-Hähnlein, Germany

[73] Assignee: Kao Corporation, Japan

[21] Appl. No.: 08/890,351

[22] Filed: Jul. 9, 1997

[30] Foreign Application Priority Data

Jul. 15, 1996 [DE] Germany ............ 196 28 500
Oct. 1, 1996 [DE] Germany ............ 196 40 597

[51] Int. Cl.⁶ .................................. A61K 7/13
[52] U.S. Cl. .......... 8/426; 8/602; 8/606; 8/901; 8/913; 8/914; 8/915
[58] Field of Search ............ 8/405, 426, 435, 8/606, 654, 655, 657, 658, 659, 900, 901, 913, 914, 915, 525, 602

[56] References Cited

U.S. PATENT DOCUMENTS

| | | | |
|---|---|---|---|
| 3,100,739 | 8/1963 | Kaiser et al. | 8/426 |
| 3,194,735 | 7/1965 | Brechner | 8/426 |
| 3,951,598 | 4/1976 | Arashi et al. | 8/913 |
| 4,240,450 | 12/1980 | Grollier et al. | 8/404 |
| 4,526,701 | 7/1985 | Rubin | 8/525 |
| 4,943,430 | 7/1990 | Hefford et al. | 8/405 |
| 5,254,333 | 10/1993 | Kajino et al. | 8/405 |
| 5,332,581 | 7/1994 | Yoshihara et al. | 8/429 |
| 5,376,146 | 12/1994 | Casperson et al. | 8/405 |
| 5,422,031 | 6/1995 | Nomura et al. | 8/435 |
| 5,665,334 | 9/1997 | Raspanti et al. | 424/59 |
| 5,683,685 | 11/1997 | Hirano et al. | 424/70.83 |
| 5,750,099 | 5/1998 | Yoshihara et al. | 424/70.17 |

FOREIGN PATENT DOCUMENTS

| | | |
|---|---|---|
| 137178 | 4/1985 | European Pat. Off. . |
| 367926 | 5/1990 | European Pat. Off. . |
| 503507 | 9/1992 | European Pat. Off. . |
| 5-43437 | 2/1993 | Japan . |

OTHER PUBLICATIONS

Derwent Abstract of JP 61–192,780, Toyota Cent Res & Dev Lab, Aug. 1986.

*Primary Examiner*—Caroline D. Liott
*Attorney, Agent, or Firm*—Londa and Traub LLP

[57] ABSTRACT

Stable compositions for dyeing of human hair in an aqueous carrier, providing durable, light-fast hair colorations, comprising a) 0.0001% to 2.5% by wt. of at least one cationic directly acting hair dyestuff;
b) 0.1% to 10% by wt. of at least one zwitterionic (amphoteric) surfactant; and
c) 0.1% to 5% by wt. of at least one water-soluble UV-absorbing compound bearing an anionic group, all percentages calculated to the total composition.

12 Claims, No Drawings

COMPOSITION FOR DYEING HUMAN HAIR COMPRISING A CATIONIC DYE, A ZWITTERIONIC SURFACTANT, AND AN ANIONIC UV-ABSORBER

BACKGROUND OF THE INVENTION

This invention comprises a composition for dyeing of human hair providing superior stability and simultaneously a hair coloration with improved coloring intensity.

It is generally known that hair dyeing compositions are classified into two categories, i.e., on the one hand permanent dyeing compositions comprising oxidizing hair dyestuff precursors, which, together with oxidizing agents, develop the desired hair coloration depending on the formula chosen; and, on the other hand, semipermanent hair dyeing compositions comprising direct dyes which do not require any addition of an oxidizing agent to develop their dyeing effect. Accordingly, these dyeing results are less permanent than those obtained with permanent dyeing compositions.

These dyeing compositions on the basis of direct dyes are usually applied either as tinting shampoos, lotions or color setting lotions, optionally also as aerosol foam preparations.

The direct dyes used therein are normally of the cationic type; rinsing compositions also contain cationic surfactants, particularly quaternary ammonium salts, as additional essential ingredients.

The dyeing intensity and permanence achieved with these compositions is, however, not always satisfactory. A possibility for improvement of light fastness is the addition of UV-absorbers to the hair dyeing compositions to protect the hair from light damaging.

The water-insoluble UV-absorbers normally used for this purpose, however, are not suitable in this respect, as they do not adhere to the hair substantially.

Water-soluble UV-absorbers with anionic groups are known per se. Due to their substantivity they are generally suitable to improve the light fastness of hair treated with dyes containing direct-acting dyestuffs.

However, it has not been possible to incorporate these water-soluble UV-absorbing, anionic groups containing compounds into usual cationic direct-acting hair dyestuff compositions, as obviously an interaction took place between the two substances leading to an instable composition.

SUMMARY OF THE INVENTION

It has now been found, and this is the object of this invention that stable hair dyeing compositions on an aqueous basis, containing direct-acting cationic hair dyestuffs can be obtained which produce on the hair lustrous, durable, expressive and light-stable colorations, by the addition of a combination of 0.1% to 5% by wt. of at least one water-soluble, an anionic group, particularly a sulfo, carboxyl, or phosphate group bearing UV-absorbing agents, and 0.1% to 10% by wt. of at least one zwitterionic surfactant, particularly a betaine and (or) a sulfobetaine, all percentages calculated to the total composition.

DETAILED DESCRIPTION OF THE INVENTION

Within the scope of the invention, zwitterionic surfactants are especially alkyl amidobetaines of the general formula

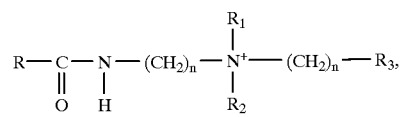

wherein R stands for a $C_8$–$C_{18}$-alkyl group, e.g., a coco group; $R_1$ and $R_2$ are lower $C_1$–$C_4$-alkyl- or hydroxyalkyl groups, particularly methyl, ethyl, and (or) hydroxyethyl groups; $R_3$ denotes a $COO^-$ or $—SO_3^-$ group; and n is 1 to 3. Betaines of the general formula

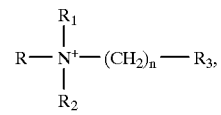

wherein R, $R_1$, $R_2$, $R_3$ and n have the same meaning as before, are also preferred ingredients.

Such betaines are, e.g., those of the formulae

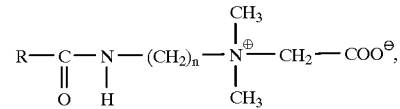

and (or)

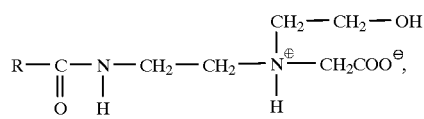

a sulfobetaine of the formula

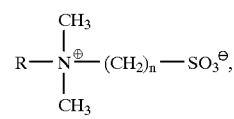

and a betaine of the formula

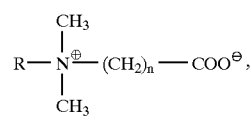

wherein R represents a $C_8$–$C_{18}$-alkyl group and n is 1 to 3.

Particularly useful are trade products such as "Tegobetaine™", "Dehytons™" such as "AB 30", "G" and "K", "Lonzaine™", "Varion™" such as "ADG" und "CAS", "Lexaine™", "Chembetaine™", "Mirataine™", "Rewoteric™", "Schercotaine™", "Monteine LCQ™"; "Alkateric™", "Amonyl™", "Amphosol™", "Cycloteric BET™", "Emcol™", "Empigen™", "Mackam™", "Monateric™", "Unibetaine™" and "Velvetex™".

Other preferred zwitterionic (amphoteric) surfactants are those selected from the group of $C_8$–$C_{18}$-alkyl hydroxysulfobetaines, a carboxymethyl $C_8$–$C_{18}$-alkyl polypropyl amine, and/or a compound of the formula

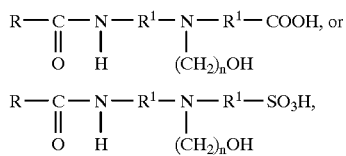

wherein R is a $C_8$–$C_{20}$-alk(en)yl group, especially a $C_8$–$C_{14}$-alkyl group, $R^1$ is an optionally hydroxysubstituted straight or branched-chain alkylene group with 1 to 3 carbon atoms and n is 1 to 3, and the water-soluble salts thereof.

Preferred are sodium caproamphoacetate, sodium caproamphopropionate, sodium caproamphohydroxypropyl sulfonate, sodium cocoamphopropionate and -acetate, sodium cocoamphohydroxypropyl sulfonate, sodium isostearoamphoglycinate, and sodium carboxymethyl methyl cocopolypropyl amine of the formula

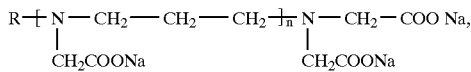

wherein R is a cocoalkyl group and n is preferably 1 to 4.

Zwitterionic surfactants are preferably present in a proportion from 0.25% to 7.5% by wt., particularly from 0.5% to 5% by wt., calculated to the total composition.

The third essential ingredient of the compositions according to the invention is a water-soluble UV-absorber, which is used preferably in a proportion from 0.1% to 5%, particularly from 0.25% to 2.5% by wt., calculated to the total composition.

Particularly useful water-soluble UV-absorbers bearing anionic groups are, e.g., 5-benzoyl-4-hydroxy-2-methoxybenzene sulfonic acid (Benzophenone-4), its sodium salt (Benzophenone-5) and 2,2'-dihydroxy-4,4'-dimethoxy-3,3'-di-sulfobenzophenone or the disodium salt thereof (Benzophenone-9) as well as phenyl benzimidazole sulfonic acid (Eusolex™ 232); however, other water-soluble UV-absorbers may also be used.

The preferred weight ratio of zwitterionic surfactant to water-soluble anionic UV-absorber is optimally about 1:1 to about 3:1.

The proportion of direct-acting dyestuffs in the compositions according to the invention varies and is about from 0.0001% to about 2.5%, preferably from 0.001% to 1%, particularly 0.01% to 0.5% by wt. of the composition.

Generally all cationic dyestuffs proposed for this purpose may be used as direct-acting hair dyes.

Preferred are the hair dyes sold under the trademark Arianor cf. K. Schrader, "Grundlagen und Rezepturen der Kosmetika", 2nd Ed. (1989), p. 811.

Particularly suitable basic (cationic) dyestuffs are

Basic Blue 6, C.I.-No. 51,175;
Basic Blue 7, C.I.-No. 42,595;
Basic Blue 9, C.I.-No. 52,015;
Basic Blue 26, C.I.-No. 44,045;
Basic Blue 41, C.I.-No. 11,154;
Basic Blue 99, C.I.-No. 56,059;
Basic Brown 4, C.I.-No. 21,010;
Basic Brown 16, C.I.-No. 12,250;
Basic Brown 17, C.I.-No. 12,251;
Natural Brown 7, C.I.-No. 75,500;
Basic Green 1, C.I.-No. 42,040;
Basic Red 2, C.I.-No. 50,240;
Basic Red 22, C.I.-No. 11,055;
Basic Red 76, C.I.-No. 12,245;
Basic Violet 1, C.I.-No. 42,535;
Basic Violet 3, C.I.-No. 42,555;
Basic Violet 10, C.I.-No. 45,170;
Basic Violet 14, C.I.-No. 42,510;
Basic Yellow 57, C.I.-No. 12,719.

Of course the (additional) use of appropriate direct plant dyestuffs is also possible.

The compositions according to the invention preferably also contain at least one cationic surfactant, particularly in a proportion from 0.1% to 7.5%, preferably 0.25% to 5%, most preferably 0.5% to 2.5% by wt. of the total composition.

Suitable long-chain ammonium compounds, which may be used as cationic surfactants either alone or in admixture, are especially cetyl trimethyl ammonium chloride, dimethyl dicetyl ammonium chloride, trimethyl cetyl ammonium bromide, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris(oligooxyethyl) alkyl ammonium phosphate, cetyl pyridinium chloride, etc.

Useful quaternary ammonium salts are also those disclosed in European Patent Application No. 472,107.

On principle all quaternary ammonium compounds listed under the general name "Quaternium" in "CTFA International Cosmetic Dictionary", Fourth Ed. (1991) are suitable.

The hair dyeing compositions according to the invention may also comprise the usual ingredients in such compositions. To avoid repetition, reference is again made to K. Schrader, "Grundlagen und Rezepturen der Kosmetika", 2nd Ed. (1989), pp. 722 to 771.

Nonionic surfactants may also be used, preferably in admixture with cationic surfactants, e.g., amine oxides in a proportion from about 0.25% to about 5%, preferably from about 0.5% to about 3.5% by wt., calculated to the total composition.

Such amine oxides belong to the state of the art, e.g., $C_{12}$–$C_{18}$-alkyl dimethyl amine oxides such as lauryl dimethyl amine oxide, $C_{12}$–$C_{18}$-alkyl amidopropyl or -ethyl amine oxide, $C_{12}$–$C_{18}$-alkyl di(hydroxyethyl) or -(hydroxypropyl) amine oxide, or also amine oxides with ethylene oxide and (or) propylene oxide groups in their alkyl chains.

Useful surfactants furtheron are the well-known $C_8$–$C_{18}$-alkyl polyglucosides, particularly with a polycondensation degree from 1.2 to 3.

Not suitable and undesirable, however, is the presence of considerable amounts of anionic surfactants.

The hair dyeing compositions according to the invention may contain all ingredients usual in such aqueous compositions.

These are, e.g., synthetic or natural hair conditioning polymers, preferably in a proportion from about 0.1% to 2.5%, particularly 0.25% to 1.5% by wt., of the total composition.

Suitable cationic polymers are known, in addition to the well-known quaternary cellulose derivatives of the type "Polymer JR", particularly quaternized homo- and copolymers of dimethyl diallyl ammonium chloride, as they are on the market under the trade name "Merquat™", quaternary vinyl pyrrolidone copolymers, especially with dialkyl aminoalkyl (meth)acrylates known under the trade name "Gafquat™", copolymers polymers from vinyl pyrrolidone and vinyl imidazolinium methochloride offered on the market under the trade name "Luviquat™", polyaminopolyamide derivatives, e.g., copolymers of adipic acid dimethyl aminohydroxypropyl di-ethylene triamine sold under the name "Cartaretine™ F", and also bisquaternary long-chain ammonium compounds of the urea structure described in U.S. Pat. 4,157,388 sold on the market under the trade name "Mirapol™ A 15".

In this context, reference is also made to the cationic polymers described in German Patents Nos.25 21 960, 28 11 010, 30 44 738, and 32 17 059, and the products disclosed closed on pp. 3 to 7 of European Patent Application No. 337,354. Mixtures of different cationic polymers may also be used.

Nonionic polymers may also be used in the place of cationic polymers or in combination with these. Suitable nonionic polymers, above all, are polyvinyl pyrrolidone homo- and copolymers, particularly polyvinyl pyrrolidone alone, copolymers from vinyl pyrrolidone and vinyl acetate or terpolymers from vinyl pyrrolidone, vinyl acetate and vinyl propionate, e.g., sold by BASF under the trade name "Luviskol™". However, (co-)polymers of the various acrylic and methacrylic esters, acrylamide and methacrylamide, e.g., polyacrylamide having a molecular weight of higher than 100,000, dimethyl hydantoin formaldehyde resins, etc., may also be used. Mixtures of different nonionic polymers are of course also possible.

Suitable are also amphoteric polymers, e.g., the copolymers from N-octylacrylamide, N-butylaminoethyl methacrylate and acrylic acid sold under the name "Amphomer™".

oil, night primrose oil, jojoba oil, castor oil, or also olive oil or soybean oil, lanolin and its derivatives, also mineral oils such as paraffin oil and vaseline.

Synthetic oils and waxes, e.g., are silicone oils, polyethyleneglycols, etc.

Other suitable hydrophobic compounds are particularly fatty alcohols, preferably those with about 8 to 22 carbon atoms in the molecule such as myristyl, cetyl, stearyl alcohol, wax alcohols and fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethyleneglycol and polyglyceryl fatty acid esters such as PEG-7-glyceryl cocoate, cetyl palmitate, etc.

These hydrophobic compounds are incorporated in the compositions according to the invention in a proportion of preferably from about 0.5% to about 10%, particularly from about 1% to 7.5%, optimally from about 1.5% to 5% by wt., calculated to the total composition.

A summary of those compositions may be found in K. Schrader, l.c., pp. 798 to 815, particularly pp. 804 ff.

The dyeing compositions according to the invention are formulated as emulsions, dispersions or (optionally thickened) gel preparations and may be also packed as aerosol foams. These preparations are generally known to the expert and do not require any further explanation.

The pH-value of the hair dyeing compositions according to the invention is preferably from about 3 to 6.5, particularly from 4 to 6.

The following examples illustrate the composition of the preparations according to the invention.

Color rinses of the following composition were prepared by admixture of the ingredients.

Examples Nos.

| Ingredients | 1 | 2 | 3 | 4 |
| --- | --- | --- | --- | --- |
| 1,2-Propandiol | 3.00 | 3.00 | 3.00 | 3.00 |
| Cetyl stearyl aclohol | 1.75 | 1.75 | 1.75 | 1.75 |
| Hydroxyethyl cellulose | 0.80 | 0.80 | 0.80 | 0.80 |
| Silicone oil | 0.50 | 0.50 | 0.50 | 0.50 |
| Methyl parabene | 0.25 | 0.25 | 0.25 | 0.25 |
| Stearyl trimethyl ammonium chloride | 0.70 | 1.00 | 0.40 | 0.35 |
| Dicocoyl dimethyl ammonium chloride | — | — | 0.30 | 0.35 |
| Henna extract | 0.50 | — | — | — |
| Camomille extract | — | 1.00 | — | — |
| Nut extract | — | — | 0.50 | — |
| Corn flower extract | — | — | — | 0.50 |
| Perfume | 0.30 | 0.30 | 0.30 | 0.30 |
| Bezophenone-4 | 0.25 | 0.30 | 0.50 | 0.50 |
| Cocoamidopropyl betaine | 0.50 | 0.70 | 1.20 | 1.00 |
| Arianor Madder Red 3 | 0.08 | — | — | 0.0015 |
| Arianor Steel Blue 3 | 0.01 | — | 0.025 | 0.0065 |
| Arianor Straw Yellow 3 | 0.01 | 0.0005 | — | — |
| Arianor Sienna Brown 3 | — | 0.0001 | 0.0125 | — |
| Arianor Mahogany | — | — | 0.0125 | — |
| Water | @ 100.00% by wt. | @ 100.00% by wt. | @100.00% bywt. | @ 100.00% by wt. |
| Hair color achieved | Red | Blond | Brown | Light Blue |

The hair dyeing compositions according to the invention may comprise the usual additives, whose type and character depend on the form of application. These are fats, fatty alcohols, emulsifiers, pH-regulants, solvents and compounding agents, solubilizers, preservatives, perfumes, etc.

Useful fats and oils which also include waxes are in particular natural oils such as avocado oil, coconut oil, palm oil, sesame oil, peanut oil, whale oil, sunflower seed oil, almond oil, peach kernel oil, wheat germ oil, macadamia nut Omitting cocoamidopropyl betaine led to instable aqueous compositions, i.e., the formation of sediments after about 24 hours storage.

Replacing the anionic UV-absorber by a water-insoluble UV-absorber resulted in colorings essentially inferior in color brilliance and permanence to those achieved with the compositions according to the invention.

The following two Examples further illustrate the invention.

| Examples Nos. | 5 | 6 |
|---|---|---|
| Hydroxyethyl cellulose | 1, 00 | 1, 00 |
| Cetyl stearyl alcohol | 1, 25 | 1, 25 |
| 1,2-Propanediol | 3, 00 | 3, 00 |
| Cetyl trimethyl ammonium chloride | 0, 20 | 0, 30 |
| Dicetyl dimethyl ammonium chloride | 0, 30 | 0, 40 |
| Methyl parabene | 0, 20 | 0, 20 |
| Dimethicone | 0, 20 | 0, 20 |
| Benzophenone-4 | 0, 25 | 0, 60 |
| Lauryl hydroxysultaine | 1, 00 | — |
| Sodium carboxymethyl cocoalkyl propylamine | — | 1, 00 |
| Henna extract | 1, 00 | — |
| Camomile extract | — | 0, 50 |
| Perfume | 0, 30 | 0, 50 |
| Basic Yellow 57 | — | 0, 10 |
| HC Red 3 | 0, 10 | — |
| Citric acid | q.s. | q.s. |
| Wasser | @ 100, 00 by wt. | @ 100, 00 by wt. |
| Hair color achieved | Red with blue shade | Yellow |

Omission of the amphoteric surfactants led to an instable aqueous composition, i.e., after 24 hours storage precipitation occured.

Replacement of the anionic water-soluble UV-absorber by a water-insoluble UV-absorber resulted in colorings, which were clearly inferior to those of the invention as regards color brilliance and durability.

I claim:

1. Composition for dyeing of human hair in an aqueous medium, comprising a) 0.0001% to 2.5% by wt. of at least one cationic direct-acting hair dyestuff;

b) 0.1% to 10% by wt. of at least one zwitterionic surfactant selected from the group consisting of an alkyl amido betaine of the formula (1)

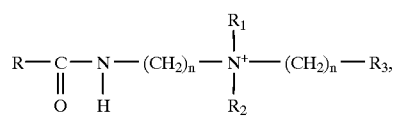

(1)

wherein R stands for a $C_8$–$C_{18}$-alkyl group; $R_1$ and $R_2$ denote a $C_1$–$C_4$-alkyl or hydroxyalkyl group; $R_3$ represents a —COO$^-$ or —SO$_3^-$ group; and n is 1 to 3;

a betaine of the formula (2)

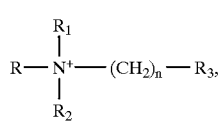

(2)

wherein R stands for a $C_8$–$C_{18}$-alkyl group; $R_1$ and $R_2$ denote a $C_1$–$C_4$-alkyl or hydroxyalkyl group; $R_3$ represents a —COO$^-$ or a —SO$_3^-$ group; and n is 1 to 3;

a compound of the formula (3)

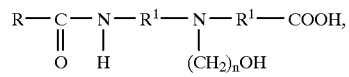

(3)

wherein R is a $C_{8\text{-}20}$-alk(en)yl group, $R_1$ is an optionally hydroxysubstituted straight chain or branched-chain alkylene group with 1 to 3 carbon atoms, and n is 1 to 3, and the water-soluble salts thereof;

a compound of the formula (4)

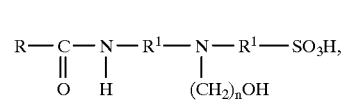

(4)

wherein R is a $C_8$–$C_{20}$-alk(en)-yl group, $R^1$ is an optionally hydroxysubstituted straight or branched-chain alkylene group with 1 to 3 carbon atoms, and n is 1 to 3, and the water-soluble salts thereof;

a carboxymethyl $C_8$–$C_{18}$-alkyl propyl amine,
and a $C_{8\text{-}18}$-alkyl hydroxysulfobetaine; and c) 0.1% to 5% by wt. of at least one water-soluble UV-absorbing compound bearing an anionic group, all precentages calculated to the total composition.

2. Composition according to claim 1, wherein the weight ratio of the zwitterionic surfactant to the water-soluble UV-absorbing compound is about 1:1 to about 3:1.

3. Composition according to claim 1, containing a zwitterionic surfactant of the formula

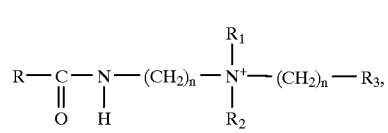

(1)

and/or a zwitterionic surfactant of the formula

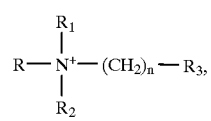

(2)

wherein R stands for a $C_8$–$C_{18}$-alkyl group; $R_1$ and $R_2$ denote a $C_1$–$C_4$-alkyl or hydroxyalkyl group; $R_3$ represents a —COO$^-$ or a —S$_3^-$ group; and n is 1 to 3.

4. Composition according to claim 1, comprising a zwterionic surfactant of the formula

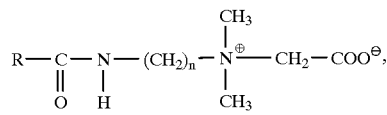

(1a)

and/or of the formula

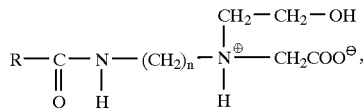
(1b)

wherein R denotes a $C_8$–$C_{18}$-alkyl group and n is 1 to 3.

5. Composition according to claim 3, comprising a zwitterionic surfactant of the formula

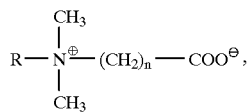
(2a)

wherein R represents a $C_8$–$C_{18}$-alkyl group and n is 1 to 3.

6. Composition according to claim 3, comprising a zwitterionic surfactant of the formula

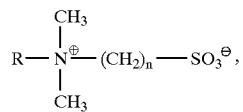
(2b)

wherein R denotes a $C_8$–$C_{18}$-alkyl group and n is 1 to 3.

7. Composition according to claim 2, comprising as zwitterionic surfactant at least one compound of the formula

(3)

(4)

wherein R is a $C_8$–$C_{20}$-alk(en)yl group, $R^1$ is an optionally hydroxysubstituted straight or branched-chain alkylene group with 1 to 3 carbon atoms, and n is 1 to 3, and the water-soluble salts thereof.

8. Composition according to claim 1, comprising as zwitterionic surfactant at least one carboxymethyl $C_8$–$C_{18}$-alkyl polypropyl amine.

9. Composition according to claim 1, comprising as zwitterionic surfactant at least one $C_8$–$C_{18}$-alkyl hydroxysulfobetaine.

10. Composition according to claim 1, having a pH-value from 3 to 6.5.

11. Composition according to claim 10, having a pH-value from 4 to 6.

12. Composition according to claim 1, containing 0.1% to 7.5% by wt., calculated to the total composition, of at least one long-chain quaternary ammonium compound.

* * * * *